United States Patent [19]

Nubel et al.

[11] 4,155,811

[45] May 22, 1979

[54] FERMENTATION PROCESS FOR THE PRODUCTION OF CITRIC ACID

[75] Inventors: Robert Nubel, Wantagh; Robert Fitts, Huntington Station; Gordon Findlay, New York, all of N.Y.

[73] Assignee: Pfizer Inc., New York, N.Y.

[21] Appl. No.: 31,903

[22] Filed: Jul. 7, 1970

Related U.S. Application Data

[63] Continuation of Ser. No. 868,897, Oct. 23, 1969, abandoned.

[51] Int. Cl.$^2$ .............................................. C12D 1/04
[52] U.S. Cl. ................................................. 195/28 R
[58] Field of Search ...................................... 195/28 R

[56] References Cited

U.S. PATENT DOCUMENTS

3,733,253   5/1973   Suzuki et al. ........................... 195/30

OTHER PUBLICATIONS

Klug et al., Applied Microbiology, vol. 15, pp. 690–693, (1967).

*Primary Examiner*—Lionel M. Shapiro
*Attorney, Agent, or Firm*—Connolly and Hutz

[57] ABSTRACT

A process for producing citric acid directly in the free acid form by aerobically fermenting an aqueous hydrocarbon-containing nutrient medium at a low pH with a new strain of the yeast, *Candida lipolytica*.

5 Claims, No Drawings

FERMENTATION PROCESS FOR THE PRODUCTION OF CITRIC ACID

This is a continuation of application Ser. No. 868,897, filed Oct. 23, 1969, now abandoned.

BACKGROUND OF THE INVENTION

This invention relates to a process for the production of citric acid by fermentation. In particular it relates to a process for the production of citric acid in the free acid form, thus permitting its direct crystallization from the fermentation broth.

Because of its ease of assimilation, palatability and low toxicity, citric acid is one of the most commonly used acids in the food and pharmaceutical industry. It is widely used as an acidulant in beverages and also as an anti-oxidant for inhibiting rancidity in fat and oils. Both the free acid and its salts are employed as buffers in the preparation of jams, jellies, and gelatin preprations, and are also used as stabilizers in various food products.

Most of the world's supply of citric acid is produced by fermentation processes, generally using selected strains of *Aspergillus niger* with carbohydrates like molasses and dextrose as the main source of assimilable carbon. While these fermentation processes with *Asperigillus niger* are attractive, many difficulties are experienced. For example, over a period of time the citric acid producing capability of the *Aspergillus niger* culture tends to degenerate. Of more inportance is the fact that the citric acid is recovered in the form of a salt, which must then be acidified and converted to the free acid. Furthermore, a relatively long period of time, generally more than 7 days, is required for production of large quantities of citric acid by such fermentations. This long fermentation time and the extra step of converting the citrate salt to the free acid are major cost factors in producing citric acid. Thus, it is obvious that the development of a rapid fermentation process for the direct production and recovery of citric acid is of considerable commercial importance.

Belgian Pat. No. 716,247 teaches a process for the production of citric acid, using as inoculants various yeasts of the genus Candida which are capable of accumulating citric acid and of assimilating hydrocarbons, and fermenting at a pH of about 4 to about 7.5 until a substantial amount of citric acid is accumulated in the broth. Here again, however, the citric acid is produced as calcium citrate and must be acidified, usually with sulfuric acid, to convert to the more desirable free citric acid.

There are other reports in the literature describing the propagation of members of the genus Candida in media containing hydrocarbons, e.g., I. Tanabe, J. Okada, and H. Ono, Agr. Biol. Chem., 30, 1175 (1966), E. J. Nyns, J. P. Auquiere, N. Chiang, and A. L. Wiaux, Nature, 215, 177 (1967); M. J. Klug and A. J. Markovetz, Appl. Microbiol., 15, 690 (1967), J. Bacteriol., 33, 1847 (1967). However, apparently no one has heretofore succeeded in producing free citric acid in such hydrocarbon systems. It is a characteristic property of most citric acid-accumulating strains of Candida that the polyhydric alcohols erythritol, arabitol and mannitol are co-produced in the fermentation broth with the citrates. An additional distinguishing feature of the present invention is that the superior citric acid-accumulating properties of the new strain of *Candida lipolytica* are accompanied by co-production of only low amounts of erythritol and at most of only traces of arabitol and mannitol. Thus, the increased concentration of citric acid, present in the free form at the low terminal pH of the fermentation broth, and the small amount of co-produced impurities, in combination, allow for the isolation of citric acid directly from the filtered fermentation broth.

SUMMARY OF THE INVENTION

The present invention now provides a process for producing citric acid by aerobically fermenting an aqueous nutrient medium containing a hydrocarbon or mixture of hydrocarbons as the principal source of assimilable carbon with a certain new strain of the genus Candida for about 4–7 days, and recovering the free acid directly by concentrating the filtered fermentation broth. In particular, this invention comprises a process for producing citric acid by aerobically fermenting *Candida lipolytica* ATCC No. 20,228 in a nutrient medium containing at least one n-alkane or n-alkene hydrocarbon of from 9 to 19 carbon atoms, which is intimately mixed with an aqueous phase containing an assimilable source of nitrogen, minerals and other usual nutrients.

In the process of this invention, no pH adjustment is generally required during the fermentation cycle, and toward the end of the fermentation, generally after the process is at least one-half to about three-fourths completed, the pH of the fermentation broth falls to about 2 to about 3. In side by side comparisons with *Candida lipolytica* IFO-1437, referred to in the aforesaid Belgian Pat. No. 716,247, the new strain of *Candida lipolytica*, ATCC No. 20,228, produces about five to ten times more citric acid. At no time during the fermentation cycle does the pH of the fermentation broth inoculated with the prior art *Candida lipolytica* strain IFO-1437 fall below 3. Surprisingly, however, it has been discovered that the pH of the fermentation broth using the new strain ATCC 20,228 need not be adjusted during the fermentation cycle, and that high yields of citric acid are accumulated at the terminal pH range of about 2 to about 3. The accumulated free citric acid is recovered directly by concentrating the filtered fermentation broth after removal of the metal ions of the buffer.

DETAILED DESCRIPTION OF THE INVENTION

It has now been found that a certain strain of the yeast *Candida lipolytica* has the peculiar ability to accumulate citric acid in the free acid form, during the aerobic fermentation of aqueous media containing a hydrocarbon as the principal or sole source of assimilable carbon, provided however that the pH of the fermentation is kept low, i.e., the citric acid is not neutralized as it is produced. At the present time only the one strain of *lipolytica* is known which permits direct crystallization of citric acid from the concentrated broth. Most publicly available strains have been tested and found not to possess this unique property. The operable strain has been deposited in a recognized public collection, the American Type Culture Collection, and given the number ATCC 20,228.

To take the fullest advantage of this property of the culture, fermentation is conducted at low pH, i.e., without neutralizing the citric acid produced. It is surprising but true that the strain No. 20,228 remains viable and a strong citric acid-producer even at pH's of about 2–3 or even lower. Initially, it is necessary to maintain a pH of about 4–7 (usually about 5–6) to permit cell growth to occur. However, after the cell mass is developed, the pH is allowed to fall naturally, as more citric acid is produced without adding more buffer or other base to react with the product. The fermentation is usually complete in 5–7 days. Before the first 2 days have passed, the pH is already below 4, and it continues to fall to a final range of about 2–3 as more acid is produced. As previously noted, this means that most of the product is already in the form of the free acid, not a citrate, and is ready to be recovered.

The initial pH maintenance could be effected by adding caustic or other base. However, it is most convenient to simply add a limited amount of a carbonate at the outset, such that its buffering capacity will have been consumed by citric acid produced at about the time that the cell mass is developed adequately to use as inoculum for the fermentation. As a buffer, it is preferred to add calcium carbonate to the medium. This reacts with the citric acid that accumulates during the growth stage, thereby preventing the pH of the medium from becoming too acidic. It is well-known that during the initial stages of yeast propagation, if the medium drops to pH less than about 4.0, the growth of the yeast cells will cease or be markedly reduced. It is also believed that some of the carbon dioxide produced in the reaction of the citric acid with calcium carbonate may be metabolized by the yeast cells and thereby promote their growth in the medium. Besides calcium carbonate one can also use barium carbonate, calcium oxide, barium oxide and other well-known buffers.

Although it is generally preferred to use n-hexadecane as the principal or sole hydrocarbon in fermentation, other n-alkanes and n-1-alkenes can be used. Mixtures of hydrocarbons can be used as well, including crude and semi-refined materials, but at least a portion should consist of a hydrocarbon having a chain length of from about 9 to 19 carbon atoms.

Generally, the hydrocarbon is employed at a concentration of about 5–9% by weight based on the medium although this aspect is not critical and a lesser or higher concentration of hydrocarbon can be used. Among the available inorganic sources of nitrogen, we favor such nitrogen salts as ammonium sulfate, ammonium chloride, and ammonium nitrate. Of the numerous organic nitrogen sources, we prefer wheat bran, soybean meal, urea, the amino acids, and peptones. We have found the commercially available NZ Amine YTT, available from the Sheffield Chemical Co., Norwich, N.Y. to be a convenient peptone source. It is, of course, well known that such vitamins as biotin and such mineral cations and anions as sodium, potassium, cobalt, phosphate, and sulfate are also beneficial to the growth of the yeasts. Most of these trace vitamins and minerals are available in the corn steep liquor, and some of the nitrogen sources, e.g., soybean meal, and therefore it is not usually necessary to add them individually to the fermentation medium.

As above indicated, the fermentation medium contains conventional sources of assimilable nitrogen, minerals, and other growth factors which are contained in the aqueous phase. A medium that has been found especially suitable is one containing an ammonium salt, corn steep liquor and hydrocarbon. The corn steep liquor can be optionally replaced with potassium dihydrogen phosphate. The hydrocarbon level should be at least about 3% by weight of the medium in order to produce any significant concentrations and yields of citric acid, and between about 5 and 20% by weight is the range generally for optimum results. The function of the water is essentially to provide a medium for the nitrogen sources, minerals, and growth factors, although some water is of course necessary to properly maintain the yeast cells. Thus while very high concentrations of hydrocarbon can be employed, e.g., 50% or even more, from a practical standpoint, optimum citric acid production is realized when the hydrocarbon level is kept within the preferred ranges.

While any form of aerobic incubation is satisfactory, controlled aeration is preferred, as for example agitation of the medium under air, or sparging of air through the medium. Since the hydrocarbon is immiscible in the aqueous phase, it is desirable to maintain it in a finely dispersed form in the aqueous medium during the fermentation, thus insuring that a large surface of the hydrocarbon will be in contact with the aqueous phase. In this manner there will be optimum contact between the yeast cells, the aqueous phase and the hydrocarbon. A preferred means of accomplishing these objectives is submerged fermentation, rapidly stirring the mixture while simultaneously passing air through it, e.g., by sparging. To insure good dispersion of the hydrocarbon, one may also include a surfactant in the medium.

The usual temperatures known in the art for growing yeasts, e.g., about 20°–37° C., may be employed, a range of from about 25° to 29° C. being preferred with fermentation times of 4 to 7 days. The initial growth period of the yeast cells, for preparation of the inoculum is preferably 24 to 48 hours. These general conditions of growth and fermentation are well known in the art, as are also methods for the recovery of the citric acid produced, e.g., centrifugation, filtration, concentration under vacuum, etc.

It is a critical feature of this invention that free citric acid is isolated directly from the filtered fermentation broth in excellent yield and purity. Because of the unique nature of the Candida strain ATCC No. 20,228, good yeast metabolism and high citric acid production are maintained as the pH of the fermentation broth drops quickly to about 2 to 3 or even lower after the fermentation is initiated. Unlike the aqueous carbohydrate-containing media used in the *Aspergillus niger* production of citric acid, or in the Candida techniques of the prior art, the sparkling filtered hydrocarbon fermentation broth of the present invention is low in impurities and almost colorless. Pure crystalline citric acid is obtained directly in recovery yields of 50°–75% or greater by simple evaporation or in vacuo concentration processes. This novel fermentation process obviates the need for continuous pH adjustment, and through the direct recovery of high purity citric acid in good yield, substantial savings are achieved by eliminating the intermediate recovery steps of salt formation and subsequent conversion to the free acid by the use of mineral acids, ion exchange or electrodialysis.

It is to be understood that the process of the present invention also embraces the use of mutants or variants of the *C. lipolytica* strain, as produced by various chemical and physical means, provided, of course, that they retain the acid-resistance and citric acid-accumulating ability of ATCC No. 20,228. Such mutants are produced by X-ray and UV radiation, treatment with nitrogen mustards or organic peroxides, and other similar techniques well known to those skilled in the art. In addition, the use of subcultures, natural mutants, variants and the like, is contemplated in carrying out the process of the present invention. The following examples are provided to illustrate the present invention, but not to limit its scope.

EXAMPLE I

A potato dextrose agar slant containing cells of *Candida lipolytica* ATCC 20,228 is transferred to a liquid medium prepared from 3.g. of NZ Amine YTT, a commercial source of assimilable nitrogen comprising peptones from the degradation of casein and available from The Sheffield Co., Norwich, N.Y., 34.7 g. of $C_{14}$-$C_{16}$n-paraffins, available from The Continental Oil Co., N.Y., N.Y. and 600 ml of tap water. The medium is first sterilized for 30 minutes at 120° C. The Candida cells are then incubated aerobically in the medium with agitation at room temperature (27° C.) for 48 hours, using a rotary shaker. At the end of that time, a 5% inoculum of the Candida growth is transferred to an aqueous sterilized nutrient medium containing, per liter of medium, 5.0 g. of corn steep liquor, 4.0 g. of ammonium sulfate, 15.0 g. of calcium carbonate and 155 g. of $C_{14}$-$C_{16}$n-paraffins. The inoculated medium is stirred for 48 hours and aerated at the rate of 4.0 S.C.F.H.G. (standard cubic feet of air per hour per gallon) at a temperature of 26° C. During this 48 hour propagation period the pH is maintained at about 5–6 to permit optimum cell development, adding more calcium carbonate buffer in small increments as needed. This limited amount of buffer is consumed as the cell mass produces citric acid, so that by the end of the 48 hours the pH is already slightly below 4 and falling quite rapidly.

A 5% aliquot of this actively growing inoculum is then added to a large fermenter containing the following ingredients per liter of sterilized medium: 4.7 g. of urea, 0.001 g. of thiamine hydrochloride, 180 g. of $C_{14}$-$C_{16}$n-paraffins and 0.375 g. of $KH_2PO_4$ (sterilized separately). The fermentation medium is stirred for 144 hours (6 days) at 1725 rpm, 4.0 S.C.F.H.G. (standard cubic feet of air per gallon per hour) and a temperature of 26° C. The fermentation yield of citric acid monohydrate is 225 grams per liter. Early in this six-day run the pH levels off of its own accord at about 2–3 and no adjustments are necessary. After the 6 days, the solids and mycelium are removed by filtration and the filtered fermentation broth concentrated under vacuum at 45° C. to 40° Baume. The crystals of citric acid which are formed after standing overnight are removed by centrifugation. Second and third crops of citric acids are recovered by concentrating the mother liquors under vacuum to 45° Baume at 75° C. The total recovery of free citric acid is approximately 50% by weight. Residual product in the final mother liquor is lastly recovered as the monosodium salt by neutralizing with sodium hydroxide and concentrating under vacuum.

EXAMPLE II

The process of Example I is repeated replacing the $C_{14}$-$C_{16}$n-paraffins in the final fermenter medium with n-hexadecane, with comparable results. After recovery of the free citric acid, the residual mother liquor is again neutralized with sodium hydroxide and concentrated under vacuum, and the remaining citric acid recovered as the trisodium salt.

EXAMPLE III

The process of Example I is repeated with the exception that in the final fermenter stage the $C_{14}$-$C_{16}$n-paraffins are replaced with a mixture of 28.9 g each of the following hydrocarbons: n-decane, n-nonane, n-udecane, n-tridecane, n-pentadecane, n-hexadecane and n-octadecane. Comparable results are obtained, i.e., better than 50% recovery of the free citric acid. The final mother liquor is thereafter adjusted to pH 8–10, and sufficient calcium chloride is added to convert all the residual citric acid to calcium citrate which is recovered by centrifugation.

EXAMPLE IV

A liquid nutrient medium is prepared from 150 g. of Cerelose, a corn steep available from Corn Products Sales Co., N.Y., N.Y., 15 g. of peptone, 5 g. of yeast extract, 4 g. of sodium chloride, and 1 liter of water. After sterilization this medium is inoculated with cells of *Candida lipolytica* ATCC 20,228 and incubated with agitation at room temperature under submerged aerobic conditions for 24 hours. At the end of this time, the pH is about 6.5. The Candida cell content of the medium (spindown) is determined by centrifuging a 15 ml. sample of the medium at 2000 g. for 15 minutes. When a density of 0.5 ml. of cells per 15 ml. of growth medium is realized, the cell suspension is used to inoculate the appropriate fermentation medium.

Several ml. of this 24 hour-old inoculum are added to an aqueous, sterilized nutrient medium containing per liter the following ingredients: 4.7 g. of urea, 0.01 g. of thiamine hydrochloride, 0.1 g. of $MgSO_4$, 7 $H_2O$, 180 g. of $C_{14}C_{16}$n-paraffins (Continental Oil Company) and 0.75 g. of $KH_2PO_4$ (sterilized separately).

The fermentation medium is stirred for five days at 1725 rpm, with aeration of 4.0 cubic feet of air per hour per gallon, and a temperature of 25° C. The pH drops within the first two days from about 6.5 to about 2.5 and stabilizes itself at 2.0–2.5. The solids and mycelium are removed by filtration after the 5-day period. The filtered broth is concentrated under vacuum at 45° C. to 40° Baume. After seeding with crystals of citric acid and standing overnight, the free citric acid crystallizes out and the crystals are removed by centrifugation. Second and third crops of citric acid are recovered by further concentrating the mother liquor to 45° Baume at 75° C. The residual liquor is lastly partially neutralized with sodium hydroxide and concentrated under vacuum, and the remaining citric acid recovered as the monosodium salt.

EXAMPLE V

The procedure of Example IV is repeated replacing the $C_{14}C_{16}$n-paraffins with a hydrocarbon mixture, NP-200, composed of n-paraffins having from 9 to 19 carbon atoms and available from the Union Carbide Company, N.Y., N.Y. After 138 hours of fermentation, the free citric acid in better than 50% yield is recovered by the same method. Potassium hydroxide is added this time to the residual mother liquor and the solution concentrated under vacuum to recover remaining citric acid as the monopotassium salt.

What is claimed is:

1. In a process for producing citric acid by fermenting a yeast belonging to the genus Candida, capable of accumulating citric acid and of assimilating hydrocarbons, in an aqueous nutrient medium containing at least one normal paraffin having from about 9 to 19 carbon atoms as the principal source of assimilable carbon, the improvements which comprise in combination employing as the fermentation inoculum an actively growing culture of *Candida lipolytica* ATCC No. 20,228, and conducting the major part of the fermentation at a pH substantially below 4.

2. The process of claim 1 wherein the said pH is between about 2 and 3.

3. The process of claim 1 wherein the fermentation is conducted for between about 4 and 7 days.

4. The process of claim 1 wherein the citric acid product is recovered as the free acid directly from the filtered fermentation broth.

5. The process of claim 1 wherein the said inoculum is first prepared by growing *Candida lipolytica* ATCC No. 20,228 in an aqueous nutrient medium at a pH between about 4 and 8 for between about 1 and 2 days.

* * * * *